United States Patent [19]

Tsuyoshi et al.

[11] Patent Number: 4,843,874
[45] Date of Patent: Jul. 4, 1989

[54] METHOD OF CHECKING THE WORKMANSHIP OF PAINT COATING

[75] Inventors: Nagata Tsuyoshi; Fujita Katsuto, both of Osaka; Okuda Shinji, Hyogo, all of Japan

[73] Assignee: Sunstar Engineering Inc., Osaka, Japan

[21] Appl. No.: 173,070

[22] Filed: Mar. 24, 1988

[30] Foreign Application Priority Data

Mar. 27, 1987 [JP] Japan .................. 62-75146

[51] Int. Cl.$^4$ ............ G01B 21/00; G01N 21/25
[52] U.S. Cl. ................. 73/150 R; 356/406; 356/425; 427/10
[58] Field of Search .......... 73/150 R; 356/406, 425; 118/665, 691, 712; 427/10

[56] References Cited

U.S. PATENT DOCUMENTS

| | | | |
|---|---|---|---|
| 3,376,426 | 4/1968 | Frommer et al. | 73/150 |
| 3,737,239 | 6/1973 | Adams et al. | 356/406 |
| 3,748,046 | 7/1973 | Murray | 356/425 |
| 3,756,725 | 9/1973 | Manring | 356/425 |
| 3,819,948 | 6/1974 | Iijima et al. | 118/665 |
| 3,890,048 | 6/1975 | Abbondio et al. | 356/425 |
| 4,372,674 | 2/1983 | Yukawa et al. | 118/691 |
| 4,518,258 | 5/1985 | Broersma | 356/406 |
| 4,527,897 | 7/1985 | Okabe | 356/406 |
| 4,652,136 | 3/1987 | Harjunmaa | 356/425 |

FOREIGN PATENT DOCUMENTS

| | | | |
|---|---|---|---|
| 2832382 | 2/1980 | Fed. Rep. of Germany | 356/406 |
| 0023587 | 2/1979 | Japan | 356/425 |
| 0186722 | 9/1985 | Japan | 356/425 |
| 0104232 | 5/1986 | Japan | 356/425 |
| 1109200 | 8/1984 | U.S.S.R. | 118/691 |
| 1133487 | 1/1985 | U.S.S.R. | 356/425 |

Primary Examiner—William A. Cuchlinski, Jr.
Assistant Examiner—Thomas B. Will
Attorney, Agent, or Firm—Koda and Androlia

[57] ABSTRACT

For checking the workmanship of paint coating, light is shed on the portion of the surface of an object where a paint has been applied. The intensity of light reflected by this portion of the surface gives a clue to a judgment on the acceptability of the paint coating. The judgment is passed by checking whether or not the above-mentioned intensity of light falls within a preset level. The level to be preset is variable according to the intensity of light reflected by the surface, the intensity of light in this case being measured prior to the application of the paint. The light reflected by the portion of the surface where the paint has been applied is resolved into three colors. A checkup is carried out on whether or not the sum of the intensities of light representing these three colors corresponds to a level preset for the amount of this sum. A level to be preset is selected from among data stored in a memory. These data are compiled beforehand according to the intensities of light reflected by the surfaces of various objects. In this case, the intensities of light are measured prior to the application of the paints.

5 Claims, 2 Drawing Sheets

METHOD OF CHECKING THE WORKMANSHIP OF PAINT COATING

BACKGROUND OF THE INVENTION

The present invention relates to a method of checking the workmanship of paint coating, such as primer coating, done to the peripheral areas of the windshield, rear window glass, etc. of an automobile or the coupling flanges, etc. of an automobile chassis.

Prior to glazing a window in the process of assembling an automobile, it is most common to apply a sealant to the whole periphery of each window glass such as a windshield and a rear window glass. Prior to applying the sealant, it is also common to apply a black primer to the window frame and to the portion of each window glass where the sealant is to be applied. The aim of the black primer coat is to obtain a reliably sealed condition.

Various manipulators are available for the automatic application of the sealant and the black primer.

The fluidity and surface condition of these paints remarkably differ with ambient temperatures and with whether or not these paints are in touch with air. The workmanship of paint coating is affected by the paint discharge rate and paint coating speed. It is comparatively difficult, therefore, to quantitatively control the paint discharge rate and uniformly apply a paint to the surface of an object to be coated therewith.

For this reason, the workmanship of paint coating is not always found to be normal, but is occasionally found to be defective. For example, lack of hiding occurs when the primer film thickness is insufficient, and stringiness occurs when the quantity of the primer is insufficient.

It is known to use a reflection type photoelectric sensor in a method of checking the workmanship of paint coating. In this known method, a checkup is carried out on whether or not the intensity of light reflected by the surface of a coat of paint falls within a preset level.

The trouble is that the workmanship of paint coating cannot always be checked accurately by this known method. Whether or not it can be checked accurately by this known method depends on the intrinsic condition of the surface of an object to be coated with the paint.

The criterion for judging the workmanship of, e.g., primer coating as coming up to the standard consists in whether or not the coat of primer has a prescribed width.

From this criterion, the following trouble results: If stringiness or lack of hiding occurs in some portions of the coat of primer, the surface of the object coated with the primer is exposed in these portions. Consequently, even if the coats of primer have an equal width, the intensity of reflected light incident on a photoelectric sensor differs with the colors of other intrinsic conditions of the surfaces of objects.

From the foregoing, it will be apparent that the reason for the workmanship of primer coating being not always checked accurately by the above-described conventional method is that, according to the difference in the intrinsic conditions of the surfaces of objects, the conventional method may possibly pass different judgments on two primer coatings applied respectively to the surfaces of two objects, even if these two primer coatings are of the same workmanship according to the above-mentioned criterion.

To put it concrete, let it be supposed that a black primer is applied to a white surface and a blue surface, that these two primer coatings are of the same workmanship, and that lack of hiding occurs in the same manner in these two coats of primer. Then the light reflected by the portions of the white surface in which the lack of hiding has occurred is stronger than the light reflected by the portions of the blue surface in which the lack of hiding has likewise occurred. Thus the intensity of reflected light incident on a photoelectric sensor differs with the intrinsic conditions of the surfaces of objects.

If the above-mentioned two coats of black primer, which are of the same workmanship, are subjected to a judgment on the acceptability on the basis of the same preset level, the black primer applied to the white surface will be judged to be unacceptable, while the black primer applied to the blue surface will be judged to be acceptable.

SUMMARY OF THE INVENTION

Under these circumstances, it is an object of the present invention to provide a method by which the workmanship of paint coating can be checked accurately irrespective of a difference in the intrinsic surface conditions of objects to be coated with a paint such as a black primer.

In brief, the present invention resides in making a preset level variable according to the intensities of light reflected by the surfaces of objects which are going to be coated with a paint. A level to be preset is selected from among data stored in a memory. For retrieving an optimum level from this memory, the light reflected by the surface of an object which is going to be coated with a paint is resolved into three colors. In the next step, digital values obtained in proportion to the intensities of light representing respective colors are summed up. In a further step, a level corresponding to the sum of the intensities of light representing these three colors is selected.

The above-mentioned and other objects of the present invention are more fully set forth in the following detailed description of a presently preferred embodiment of the present invention, which description is presented with reference to the accompanying drawings.

DESCRIPTION OF A PREFERRED EMBODIMENT

Figure 1:
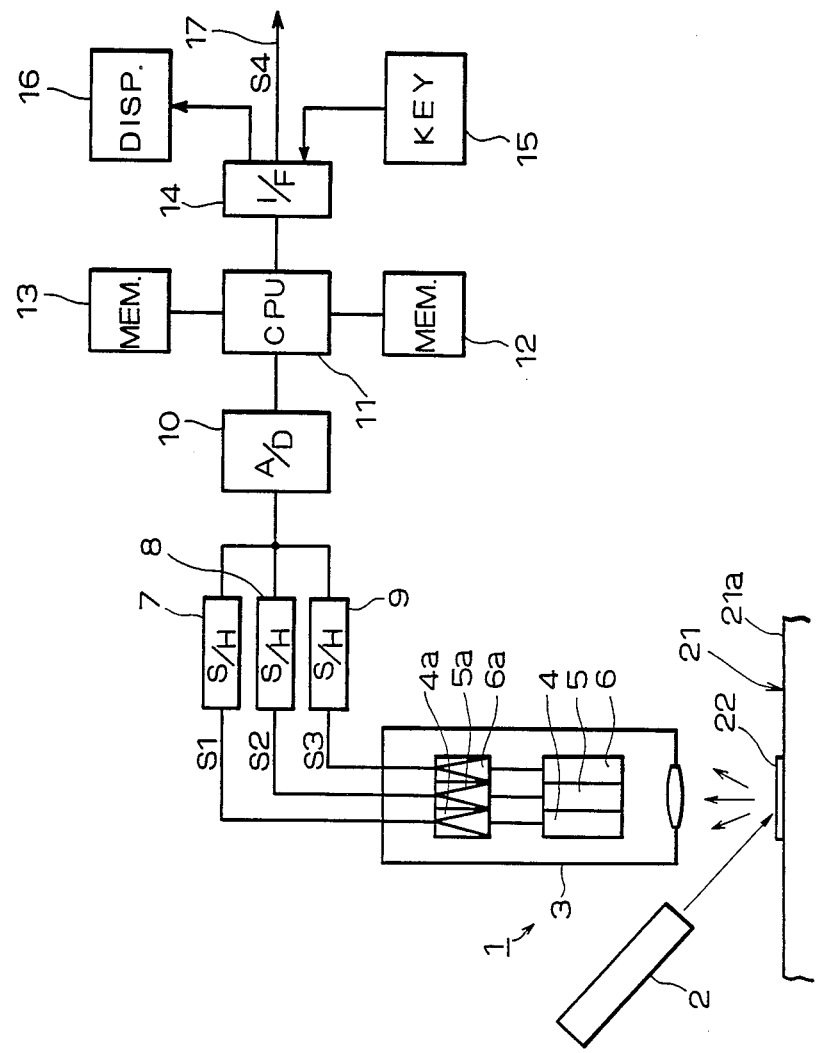
FIG. 1 is a block diagram of an apparatus suitable for use in the method in accordance with the present invention.

Referring now to FIG. 1, a photoelectric sensor 1 consists of a light projector 2 and a light receptor 3. The light projector 2 sheds light on a primer 22 which is undergoing a checkup. The light, which is shed on the primer 22, is reflected by the surface thereof, diffused, and directed towards the light receptor 3.

The light receptor 3 includes color discrimination elements 4, 5 and 6 for detecting primary colors of the light and amplifiers 4a, 5a and 6a for amplifying the detection signals taken from the color discrimination elements 4, 5 and 6 respectively. The color discrimination elements 4, 5 and 6 consist of color filters, such as red, green and blue ones respectively, and photodiodes. In the color discrimination elements 4, 5 and 6, the light reflected by the primer 22 is resolved into three colors X, Y and Z, which approximate to color matching functions. The output signals taken from the color discrimination elements 4, 5 and 6 are amplified by the amplifiers 4a, 5a and 6a respectively, which develop detection signals S1, S2 and S3 respectively in proportion to the intensities of light representing respective colors.

The detection signals S1, S2 and S3 are fed to sample-and-hold circuits 7, 8 and 9 respectively at a sampling period of several tens of milliseconds by way of example, held therein as analog values, converted one after another into digital values in an analog-to-digital converter 10, and stored in prescribed locations in a memory 12 through a central processing unit 11.

A keyboard 15 is used to input data to the central processing unit 11 through an interface 14. Signals and other data are processed in the central processing unit 11, and the result of processing is displayed on the screen of a display unit 16 on one hand, and outputted as a control signal S4 through an output lead wire 17 on the other hand. A memory 13 stores a program that tells the central processing unit 11 what operations are to be performed. The memory 13 further stores other information such as a preset level within which the intensity of light representing each color should fall.

Figure 2:
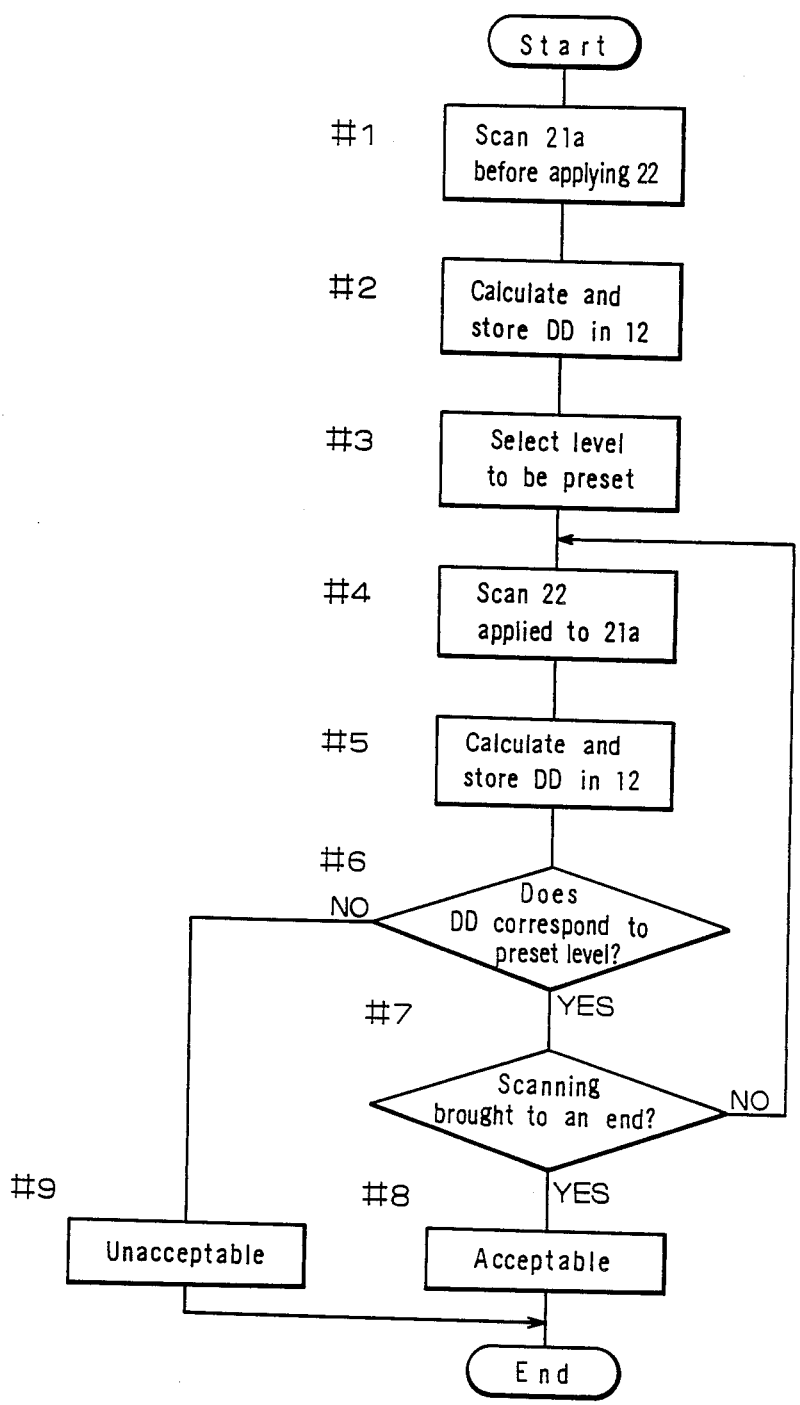
FIG. 2 is a flow chart of a program for carrying out the method by means of the apparatus shown in FIG. 1.

The operation of the central processing unit 11, hence the method in accordance with the present invention, will now be described with reference to the flow chart shown in FIG. 2.

The aim of Step 1 is to detect the condition, especially the color, of the surface 21a of an object 21 to be coated with a paint. This aim is achieved by scanning the surface 21a by means of the photoelectric sensor 1 before the primer 22 is applied to the surface 21a. Alternatively, the photoelectric sensor 1 may scan the portion of the surface 21a which is left uncovered with the primer 22 after the application thereof.

Then in Step 2, the detection signals S1, S2 and S3 obtained from the scanning in Step 1 are held in the sample-and-hold circuits 7, 8 and 9 respectively, converted into digital values D in the analog-to-digital converter 10, and stored in the memory 12. The sampling mode in this Step may be effected either once for all at an opportune moment or several times or more. In the latter case, the average of the digital values stored in the memory 12 may be found.

The aim of Step 3 is to select a level to be preset in accordance with the condition of the surface 21a of the object 21 digitalized by the above-described sampling action.

In order to achieve this aim, the digital values D representing the detection signals S1, S2 and S3 are summed up in Step 2, and the sum of the digital values D is denoted by the letters DD. When the surface of reflection is white, it is indicated by a sum DD of 100. When the surface of reflection is black (e.g., when the coat of black primer 22 is perfect), it is indicated by a sum DD of 0. The level to be preset in accordance with the condition of the surface 21a is determined by the amount of the sum DD. Table 1 shows an example of the relationship between the levels to be preset and the amounts of the sums DD. These data are stored in the memory 13.

TABLE 1

| Sum DD of digital values representing the condition of surface 21a | Level to be preset |
| --- | --- |
| 100 to 81 | 0 to 8 |
| 80 to 61 | 0 to 7 |
| 60 to 41 | 0 to 6 |
| 40 to 21 | 0 to 5 |

Let it be supposed that the condition of the surface 21a turns out to be indicated by a sum DD of 70 in Step 2. Then, it will be apparent from Table 1 that the preset level to be selected in Step 3 is 0 to 7.

Then in Step 4, the portion of the surface 21a which is coated with the primer 22 is scanned by means of the photoelectric sensor 1. Then in Step 5, the detection signals S1, S2 and S3 obtained from the scanning in Step 4 are held in the sample-and-hold circuits 7, 8 and 9 respectively, and a sum DD obtained in the same manner as mentioned above is stored in the memory 12.

In Step 4, the photoelectric sensor 1 may scan the portion of the surface 21a to which the primer 22 has already been applied. Alternatively, the work of applying the primer 22 to the surface 21a may be accompanied closely by the scanning motion of the photoelectric sensor 1.

Then in Step 6, a checkup is carried out on whether or not the sum DD obtained in Step 5 as the one indicating the condition of the primer 22 corresponds to the preset level selected in Step 3, i.e., to the range between 0 and 7. If the result of the checkup is that the sum DD corresponds to the preset level, the processings of Steps 4, 5 and 6 are repeated until the scanning motion of the photoelectric sensor 1 is brought to an end in Step 7, whereupon the workmanship of primer coating is judged to be acceptable in Step 8.

Contrariwise, the workmanship of primer coating is judged to be unacceptable in Step 9 if the result of the checkup carried out in Step 6 is that the sum DD does not correspond to the preset level. The judgment passed in Step 8 or 9 is displayed on the screen of the display unit 16. A control signal S4 developed on the basis of this judgment is outputted through the output lead wire 17.

By way of a second example, the level to be preset is 0 to 5 if the condition of the surface 21a of an object 21 turns out to be indicated by a sum DD of 30 in Step 2. The level of 0 to 5 is narrower than the level of 0 to 7 hereinbefore presented for the purpose of giving the first example. The reason for the narrower level is that the surface 21a of the second example has a darker color than the surface of the first example. Consequently, even if stringiness or lack of hiding occurs in the same manner in the primers 22 applied to these two surfaces, the light reflected by the surface of the second example is weaker than the light reflected by the surface of the first example. Consequently, the sum DD obtained as the one indicating the condition of the primer 22 applied to the surface of the second example is smaller.

The keyboard 15 may be used to input data shown in Table 1. These data are based on the results of tests conducted beforehand with various objects 21 and primers 22.

In the above-described embodiment, the sum DD of the digital values D is used for selecting a preset level to be applied to all the colors included in the light reflected by the primer 22. Instead of using the sum DD, however, one of the digital values D may be used for the same purpose. Alternatively, each of the digital values D may be used for selecting a preset level to be applied to each color included in the light reflected by the primer 22.

In the above-described embodiment, levels to be preset are predetermined on the basis of the results of tests conducted on the surfaces 21a of various objects 21. However, a change in the sum DD may be used as a clue to the detection of a change in the intensity of light reflected by the surface of a coat of paint. Alternatively, a level to be preset may be determined by operations performed with digital values D or sum DD, since either of them may be regarded as mirroring the intrinsic condition of each surface 21a. Furthermore, the digital values D and the sum DD per se may be determined in a different manner from the foregoing according to how many bits the analog-to-digital converter 10 and the memory 12 can handle or according to the capacity of the central processing unit 11. The hardware of, and the procedures for the operations of, the apparatus shown in FIG. 1 may be varied or altered without departing from the spirit of the present invention and the scope of the appended claims.

What is claimed is:

1. A method of checking the workmanship of paint coating comprising:

applying light onto surfaces of an object;

measuring an intensity of light reflected by the surfaces of said object before paint is applied thereon;

determining a preset level in response to the measured intensity of light which is reflected from the unpainted surfaces of the object;

measuring the intensity of light reflected from the surfaces of the object after paint has been coated thereon; and determining if said measured intensity of light which is reflected from the painted surfaces of the object is within said preset level.

2. A method according to claim 1, wherein:

the light reflected by the unpainted and painted surfaces is resolved into three colors;

the intensity of the light representing each of said three colors of the unpainted and painted surfaces is summed, respectively, and the preset level determined in response to the sum of the intensities of light from the unpainted surfaces; and whether or not said sum of the intensities of the painted surfaces falls within the preset level is determined.

3. A method according to claim 1 or 2, wherein a single level is selected from a plurality of levels stored in a memory as the preset level in response to the intensity of the light reflected by the unpainted surfaces of the object.

4. A method according to claim 1, wherein said light reflected by the paint surfaces of the object is a reflected light which is diffused from said painted surfaces.

5. A method according to claim 1, wherein:

the intensity of the light reflected by the unpainted surfaces of the object is resolved into three colors and measured;

three different preset levels are determined in response to the intensity to each of the three colors;

the light reflected by said painted surfaces is resolved into three colors; and whether or not the intensity of each of said three colors falls within a corresponding one of said preset levels is determined.

* * * * *

UNITED STATES PATENT AND TRADEMARK OFFICE
CERTIFICATE OF CORRECTION

PATENT NO. : 4,843,874
DATED      : July 4, 1989
INVENTOR(S): TSUYOSHI NAGATA; KATSUTO FUJITA, et al It is certified that error appears in the above-identified patent and that said Letters Patent is hereby corrected as shown below:

Title page,

Item [75] Inventors: Change "Nagata Tsuyoshi; Fujita Katsuto, both of Osaka; Okuda Shinji, Hyogo, all of Japan" to --Tsuyoshi Nagata; Katsuto Fujita, both of Osaka; Shinji Okuda, Hyogo, all of Japan--

Signed and Sealed this

Twenty-sixth Day of June, 1990

*Attest:*

HARRY F. MANBECK, JR.

*Attesting Officer*     *Commissioner of Patents and Trademarks*